United States Patent [19]

Baker

[11] Patent Number: 5,078,783
[45] Date of Patent: Jan. 7, 1992

[54] SUBSTITUTED ALKYL CARBAMATES AND THEIR USE AS HERBICIDES

[75] Inventor: Don R. Baker, Orinda, Calif.

[73] Assignee: Imperial Chemical Industries plc, Millbank, England

[21] Appl. No.: 569,685

[22] Filed: Aug. 20, 1990

[51] Int. Cl.$^5$ .............................................. A01N 37/34
[52] U.S. Cl. ........................................ 71/105; 71/106;
558/417; 560/160; 560/161; 560/164
[58] Field of Search ...................... 560/160, 161, 164;
558/417; 71/105, 106

[56] References Cited

U.S. PATENT DOCUMENTS

| | | | |
|---|---|---|---|
| 3,439,021 | 4/1969 | Fancher | 71/106 |
| 3,767,699 | 10/1973 | Albright | 560/164 |
| 4,080,470 | 3/1978 | Karrer | 71/106 |

FOREIGN PATENT DOCUMENTS

| | | | |
|---|---|---|---|
| 2220M | 4/1962 | France | 560/164 |
| 47-3755 | 2/1972 | Japan | 71/106 |

OTHER PUBLICATIONS

"Hackh's Chemical Dictionary", p. 4th Ed, p. 27 (1969).

*Primary Examiner*—Michael L. Shippen
*Attorney, Agent, or Firm*—Michael J. Bradley

[57] ABSTRACT

Substituted 1-alkyl carbamates of the formula

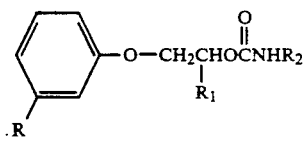

in which:
R is a member selected from the group consisting of halogen, trifluoromethyl, cyano, $NO_2$ and $C_1$–$C_3$ haloalkyloxy;
$R_1$ is selected from the group consisting of $C_1$–$C_4$ alkyl and $C_1$–$C_4$ haloalkyl; and
$R_2$ is selected from the group consisting of H, $C_1$–$C_4$ alkyl, $C_1$–$C_4$ alkoxy, $C_1$–$C_4$ alkoxyalkyl, $C_1$–$C_4$ haloalkyl and $C_1$–$C_4$ alkenyl;

and their use as herbicides is disclosed herein.

18 Claims, No Drawings

SUBSTITUTED ALKYL CARBAMATES AND THEIR USE AS HERBICIDES

BACKGROUND AND SUMMARY OF THE INVENTION

This invention relates to substituted alkyl carbamates, a process for producing them and their use as herbicide intermediates. In particular, this invention relates to substituted alkyl carbamates of the formula

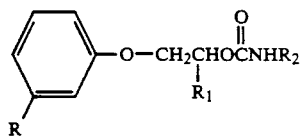

in which:

R is a member selected from the group consisting of halogen, trifluoromethyl, cyano, $NO_2$ and $C_1$–$C_3$ haloalkyloxy;

$R_1$ is selected from the group consisting of $C_1$–$C_4$ alkyl and $C_1$–$C_4$ haloalkyl; and $R_2$ is selected from the group consisting of the group consisting of H, $C_1$–$C_4$ alkyl, $C_1$–$C_4$ alkoxy, $C_1$–$C_4$ alkoxyalkyl, $C_1$–$C_4$ haloalkyl and $C_1$–$C_4$ alkenyl.

The compounds of the present invention, as will be seen from the description and test data which follows, have utility in preparing both pre-emergence and post-emergence herbicides useful against a wide range of plant species. The compounds are of particular interest when used in pre-emergence application.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn, and dwarfing. The term "herbicidally effective amount" is used to denote any amount which achieves such control or modification when applied to the undesired plants themselves or to the area in which these plants are growing. The term "plants" is intended to include germinant seeds, emerging seedlings and established vegetation, including both roots and above-ground portions.

DETAIL DESCRIPTION OF THE INVENTION AND PREFERRED EMBODIMENTS

Within the scope of the above formula, certain embodiments are preferred, as follows.

R is preferably trifluoromethyl.

$R_1$ is preferably $C_1$–$C_4$ alkyl. Particularly preferred $R_2$ groups are ethyl and methyl with ethyl being the most preferred.

$R_2$ is preferably $C_1$–$C_4$ alkyl and $C_1$–$C_4$ alkenyl.

The term "alkyl" and all groups containing alkyl portions are intended to include both straight-chain and branched-chain groups. Examples are methyl, ethyl, n-propyl, isopropyl, cyclopropyl, n-butyl, t-butyl, 2-methyl-n-butyl.

The terms haloalkyl and haloalkyloxy refer to the alkyl and alkyloxy groups, respectively, substituted by one or more halogen atoms.

The compounds of this invention are prepared by the following procedures:

A) GENERAL METHOD OF PREPARATION

1) Preparation of the Intermediate Phenoxyalcohols

The phenoxyalcohol intermediate is prepared by reaction of the appropriate phenol with the appropriate epoxide in water or dimethyl formamide using a basic catalyst. The reaction is run at the reflux temperature of the reaction mixture. Usually excess of the epoxide is required to react completely with the phenol. Potassium hydroxide at a level of 10 mole percent is convenient to use as the basic catalyst. However, other basic catalysts can also be used instead of the potassium hydroxide.

The product phenoxy alcohol separates from the reaction medium and can be worked up with aqueous base to remove unreacted phenol and then dried over a drying agent and concentrated to remove any unreacted epoxide.

2) Preparation of the Intermediate Phenoxy Chloroformates

The intermediate phenoxy chloroformates are prepared by reaction of the appropriate phenoxyalcohol with excess phosgene in an inert solvent such as methylene chloride in the presence of a catalytic quantity of dimethyl formamide. The reaction is carried out at 20°–80° C. The solvent and excess phosgene is then removed under vacuo to give the desired intermediate phenoxy chloroformate.

B) PREPARATION OF THE PHENOXY ALKYL CARBAMATES

Method 1

The product phenoxybenzyl carbamates can be prepared from the appropriate phenoxyalcohol intermediate and the appropriate isocyanate in an inert solvent such as ether, methylene chloride, or toluene. Catalysts such as 4-dimethylaminopyridine, triethylamine and/or dibutyltin dilaurate can be used. The reaction can be ran at room temperature or up to the reflux temperature of the reaction mixture. The desired product is isolated from the reaction media by evaporation under vacuum.

Method 2

The product phenoxybenzyl carbamates can be prepared by reaction of the appropriate phenoxy chloroformate intermediate with the appropriate amine in an inert solvent using an acid scavenger such as a tertiary amine or pyridine. The reaction can be ran at −20° to 40° C. The product is isolated from the reaction mixture by washing with water and dilute acid to remove the by-product amine salt followed by evaporation of the solvent to yield the desire product.

The following are examples of compounds which have been synthesized by the procedures described above. These examples are offered strictly for purposes of illustration, and are intended neither to limit nor to define the invention in any manner.

EXAMPLE 1

Preparation of 1-(3-Trifluoromethylphenoxy)-2-Butanol

A mixture of 3-trifluoromethylphenol (75 ml, 0.617 moles), 1,2-epoxybutane (58 ml, 0.617 moles), potassium hydroxide pellets (86%, 0.062 moles), and water (100 ml) were heated with stirring at 65° C. for 4 hours. At this point, more 1,2-epoxybutane (58 ml, 0.617 moles) was added and stirring at 65° C. continued overnight. The reaction was allowed to cool to room temperature and the lower phase taken off and the upper phase extracted with methylene chloride (2 ×100 ml). The organic phases were combined and washed with 5% sodium hydroxide solution (150 ml) and water (3×150 ml). This reaction solution was dried over anhydrous magnesium sulfate and stripped under vacuo to yield 138g of the desired alcohol, as determined by infra-red spectroscopy, mass spectrometry and nuclear magnetic resonance spectroscopy.

EXAMPLE 2

Preparation of O-(3-Trifluoromethylphenoxy)-2-Butylchloroformate

Phosgene (20% in toluene, 100 ml, 0.192 moles was added with stirring to the alcohol of Example 1 (30 g, 0.128 moles) and toluene (75 ml) over a period of 10 minutes with cooling using a cold water bath. Next dimethyl formamide (8 drops) was added. The reaction was heated to 50° C. at which temperature an exotherm occurred and the temperature maintained at 55° C. for 4 hours with a dry ice condenser attached to the reaction flask. The next day further phosgene (20% in toluene, 20 ml, 0.038 moles) was added and refluxing of the phosgene continued for 1½ hours to a maximum pot temperature of 80° C. Reaction mixture was cooled to room temperature and evaporated in vacuo to yield 37 g of an oil.

Gas chromatography of the product indicated 2% of the starting alcohol, 7% of an unknown impurity and 88% of the desired product.

EXAMPLE 3

Preparation of O[1-3(3-Trifluoromethyl Phenoxy)-2-Butyl] N-Allyl-Carbamate, (Compound 4)

A solution of the alcohol of Example 1 (2.34 g, 0.010 moles) ether (100 ml), allyl isocyanate (0.88 ml, 0.010 moles), triethylamine drop) and dibutyltin dilaurate (1 drop) was prepared. The reaction solution was allowed to stand at room temperature overnight. The solution was evaporated in vacuo to give an oil that was washed with hexane to give on re-evaporation 2.9 g of a thick oil. The structure was confirmed by infra-red and nuclear magnetic resonance spectrometry and mass spectrometry.

EXAMPLE 4

Preparation of O[1-(3-Trifluoromethylphenoxy)-2-Butyl]-N-Methoxyethyl-Carbamate, (Compound 10)

The chloroformate of Example 2 (2.96 g, 0.010 moles) was added to a solution of 2-methoxyethylamine (0.87 ml, 0.010 moles) and pyridine (2.42 ml, 0.030 moles) in methylene chloride (80 ml). The mixture was allowed to stand overnight and then washed with water (150 ml), 5% hydrochloric acid (100 ml), and 5% sodium bicarbonate solution (100 ml), dried over anhydrous magnesium sulfate and evaporated in vacuo to give 1.8 g of a thick oil. The structure was confirmed by infra-red spectrometry, nuclear magnetic resonance spectroscopy and mass spectrometry.

TABLE I
COMPOUNDS

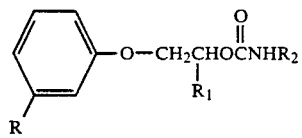

| Compound No. | R | $R_1$ | $R_2$ | m.p. °C. |
|---|---|---|---|---|
| 1 | $CF_3$ | $CH_3$ | $CH_3$ | 66.0–70.0 |
| 2 | $CF_3$ | $CH_3$ | $CH_2CH=CH_2$ | 52.5–54.5 |
| 3 | $CF_3$ | $CH_3$ | $CH_2CH_2CH_3$ | 60.0–62.0 |
| 4 | $CF_3$ | $CH_2CH_3$ | $CH_2CH=CH_2$ | Thick yellow oil |
| 5 | $CF_3$ | $CH_2CH_3$ | $CH_2CH_2CH_3$ | Semi-solid |
| 6 | $CF_3$ | $CH_2CH_3$ | $CH_3$ | Thick yellow oil |
| 7 | $NO_2$ | $CH_2CH_3$ | $CH_3$ | 63.0–66.0 |
| 8 | $NO_2$ | $CH_2CH_3$ | $CH_2CH=CH_2$ | 47.0–56.0 |
| 9 | $CF_3$ | $CH_2CH_3$ | $CH_2C\equiv CH$ | Thick Oil |
| 10 | $CF_3$ | $CH_2CH_3$ | $CH_2CH_2OCH_3$ | Thick Oil |
| 11 | $C\equiv N$ | $CH_2CH_3$ | $CH_3$ | 62.0–67.0 |
| 12 | $C\equiv N$ | $CH_2CH_3$ | $CH_2CH=CH_2$ | 56.0–62.0 |
| 13 | Br | $CH_2CH_3$ | $CH_3$ | Thick Oil |
| 14 | Br | $CH_2CH_3$ | $CH_2CH=CH_2$ | Thick Oil |
| 15 | $CF_3$ | $CH_2Cl$ | $CH_3$ | Thick Oil |
| 16 | $CF_3$ | $CH_2Cl$ | $CH_2CH=CH_2$ | Thick Oil |
| 17 | $OCHF_2$ | $CH_2CH_3$ | $CH_2CH=CH_2$ | |
| 18 | $OCF_3$ | $CH_2CH_3$ | $CH_3$ | Thick Oil |
| 19 | $OCF_3$ | $CH_2CH_3$ | $CH_2CH=CH_2$ | Thick Oil |

The compounds listed in the foregoing table were tested for herbicidal activity by various methods and at various rates for application. The results of some of these tests are given below. As one skilled in the art is aware, the results obtained in herbicidal screening tests are affected by a number of factors that are not readily controllable. Environmental conditions, such as amount of sunlight and water, soil type, soil pH, temperature and humidity, are examples of such factors. The depth of planting and the application rate of the herbicide, as well as the nature of crops being tested, can also affect the test results. Results will also vary from crop to crop and within the crop varieties.

The test procedures used are as follows:

Pre-Emergence Herbicidal Evaluation at 4 lb/acre

Planting flats were filled with sandy loam soil containing a fungicide and fertilizer. The soil was leveled and (*Cyperus esculentus*), were planted thickly enough so that several seedlings emerged per inch of row. The grassy weeds were green foxtail (*Setaria viridis*), watergrass (*Echinochloa crusgalli*) and wild oat (*Avena fatua*). Broadleaf weeds utilized were annual morningglory (*Ipomoea purpurea*), velvet-leaf (*Abutilon theophrasti*) and wild mustard (*Brassica kaber*).

Solutions of the test compounds were made by weighing out 333.0 mg of the test compound into a 60 ml wide-mouth bottle, then dissolving the compound in 25 ml of acetone containing 1% Tween ® 20 (polyoxyethlene sorbitan monolaurate emulsifier). Additional solvents, not exceeding 5 ml, were used if needed to dissolve the compound. A 20.5 ml aliquot was then taken from the solution and diluted with 25 ml of an acetone:water mixture (19:1) containing 1% Tween ® 20. This was used as the spray solution.

One day after planting, the flats were sprayed with the spray solution at a rate of 80 gallons of solution per acre with the compound being applied at a rate of 4 lb/acre (4.48 kg/hectare).

The flats were then returned to the greenhouse and watered daily by sprinkling. The degree of weed control was estimated and recorded 3 weeks after treatment, as percentage control compared to the growth of the same species in an untreated check flat of the same age.

The percent control is the total injury to the plants due to all factors, including inhibited germination, killing of the plant tissue after emergence, stunting, malformation, chlorosis, and other types of injury. The control ratings vary from 0 to 100 percent, where 0 represents no effect with growth equal to the untreated control, and 100 represents complete kill; a dash indicates that no test was performed at that level of application.

Post-Emergence Herbicidal Evaluation at 4 lb/acre

The soil was prepared and seeded with the same varieties used in the pre-emergence test. The flats were placed in the greenhouse at 70°–85° F. (21°–29° C.) and watered by sprinkling. Twelve to fourteen days after planting, the flats were sprayed at a rate of 80 gallons of solution per acre. Each compound was applied at the rate of 4 lb/acre (4.48 kg/hectare), using a spray solution prepared as in the pre-emergence test.

The flats were returned to the greenhouse after spraying and watered daily without wetting the foliage. Three weeks after treatment the degree of weed control was estimated and recorded as percentage control compared to the growth of the same species in an untreated check flat of the same age. The percent control ratings were assigned on the same basis as for the pre-emergence evaluation.

Solutions of the test compounds tested at 1.78 lb/acre (2 Kg/hectare) were made by weighing out 80 mg of the test compound into a 60 ml wide-mouth bottle, then dissolving the compound in 15 ml of acetone containing 1% Tween® 20 (polyoxyethlene sorbitan monolaurate emulsifier) and 15 ml of distilled water. Additional solvents, not exceeding 5 ml, were used if needed to dissolve the compound. This solution was used as the spray solution.

The following table lists the results of these tests, in terms of averages for the grasses and broadleaf weeds, with yellow nutsedge listed separately, in both pre- and post-emergence evaluations.

TABLE II

HERBICIDE TEST RESULTS
PERCENT CONTROL AT 4 LB/ACRE

| Compound | Pre-Emergence | | | Post Emergence | | |
|---|---|---|---|---|---|---|
| No. | YNS | AVG | AVB | YNS | AVG | AVB |
| 1 | 0 | 33 | 7 | 0 | 0 | 0 |
| 2 | 20 | 85 | 80 | 10 | 60 | 67 |
| 3 | 0 | 97 | 87 | 0 | 33 | 73 |
| 4 | 30 | 95 | 100 | 80 | 77 | 93 |
| 5 | 0 | 10 | 7 | 0 | 0 | 7 |
| 6 | 5 | 72 | 95 | 10 | 47 | 37 |
| 7 | 0 | 87 | 77 | 0 | 53 | 73 |
| 8* | 30 | 83 | 100 | 0 | 70 | 60 |
| 9 | 30 | 93 | 100 | 70 | 87 | 93 |
| 10 | 80 | 97 | 100 | 80 | 100 | 97 |
| 11 | 0 | 67 | 73 | 0 | 0 | 0 |
| 12 | 80 | 87 | 100 | 80 | 93 | 73 |
| 13 | 70 | 87 | 40 | 0 | 0 | 0 |
| 14 | 50 | 93 | 85 | 60 | 68 | 83 |
| 15* | 0 | 3 | 10 | 0 | 40 | 10 |
| 16* | 0 | 73 | 93 | 0 | 73 | 62 |
| 17* | 30 | 73 | 80 | 0 | 37 | 43 |
| 18* | 0 | 70 | 50 | 30 | 33 | 40 |

TABLE II-continued

HERBICIDE TEST RESULTS
PERCENT CONTROL AT 4 LB/ACRE

| Compound | Pre-Emergence | | | Post Emergence | | |
|---|---|---|---|---|---|---|
| No. | YNS | AVG | AVB | YNS | AVG | AVB |
| 19* | 0 | 93 | 97 | 40 | 95 | 57 |

Abbreviations:
YNS: Yellow Nutsedge
AVG: Grasses averaged
AVB: Broadleaf weeds averaged
*indicates compound tested at 1.78 lb/acre The compounds of the present invention are useful as herbicides and can be applied in a variety of ways known to those skilled in the art, at various concentrations. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as about 95% or more by weight of active ingredient. The optimum amount for any given compound will depend upon the nature of the seeds or plants to be controlled. The rate of application will generally vary from about 0.01 to about 10 lb/acre, preferably from about 0.02 to about 4 lb/acre.

Wettable powders are finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other nonvolatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound Granular formulations normally contain about 5% to about 25% active ingredients which may include surface-active agents such as heavy aromatic naphthas, kerosene or other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsules, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrenebutadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated napthalenes, xylene and other organic solvents. Pressurized sprays, wherein the active ingredient is dispersed in finely-divided form as a result of vaporization of a low boiling dispersant solvent carrier, such as the Freons, may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.5% to 15% by weight of the formulation.

The compounds of the present invention are also useful when combined with other herbicides and/or defoliants, desiccants, growth inhibitors, and the like. These other materials can comprise form about 5% to about 95% of the active ingredients in the formulations. These combinations frequently provide a higher level of effectiveness in controlling weeds and often provide results unattainable with separate formulations of the individual herbicides.

Examples of other herbicides, defoliants, desiccants and plant growth inhibitors with which the compounds of this invention can be combined are:

chlorophenoxy herbicides such as 2,4-D, 2,4,5-T, MCPA, MCPB, 2,4-DB, 2,4-DEB, 4-CPA, 2,4,5-TB, and silvex;

carbamate herbicides such as prophan, chlorpropham swep, and barban;

thiocarbamate and dithiocarbamate herbicides such as
CDEC, metham-sodium, EPTC, diallate, PEBC, and vernolate;

substituted urea herbicides such as norea, dichloral urea, chloroxuron, cycluron, fenuron, monuron, monuron TCA, diuron, linuron, monolinuron neburon, buturon and trimeturon;

symmetrical triazine herbicides such as simazine, chlorazine, desmetryne, norazine, ipazine, prometryn, atrazine, trietazine, simetone, prometone, propazine and ametryne;

chlorinated aliphatic acid herbicides such as TCA and dalapon;

chlorinated benzoic acid and phenylacetic acid herbicides such as 2,3,6-TBA, dicamba, tricamba, chloramben, fenac, PBA, 2-methoxy-3,6-dichlorophenylacetic acid, 3-methoxy-2,6-dichlorophenylacetic acid, 2-methoxy-3,5,6-trichlorophenylacetic acid and 2,4-dichloro-3-nitrobenzoic acid;

and such compound as aminotriazole, maleic hydrazide, phenylmercury acetate, endothal, technical chlordane, CDPA, diquat, erbon, DNC, DNBP, dichlobenil, DPA, diphenamide, dipropalin, trifluralin, solan, dicryl, merphos, DMPA, DSMA, MSMA, potassium azide, acrolein, benefin, bensulide, AMS, bromacil, 2-(3,4-dichloro phenyl)-4-methyl-1,2,4-oxazolidine-3, 5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, sesone, terbacil, terbutol, TCBA, alachlor, nitralin, sodium tetraborate, calcium cyanamide, S,S,S-tributylphosphorotrithioate and propanil.

These formulations can be applied to the areas where control is desired by conventional methods. Dust and liquid compositions, for example, can be applied by the use of power-dusters, boom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied the soil surface only, by spraying or sprinkling The formulations can also be applied by addition to irrigation water. This permits penetration of the formulations into the soil together with the irrigation water Dust compositions, granular compositions or liquid formulations applied to the surface of the soil can be distributed below the surface of the soil by conventional means such as discing, dragging or mixing operations.

The following are examples of typical formulations.
5% dust: 5 parts active compound, 95 parts talc.
2% dust: 2 parts active compound, 1 part highly dispersed silicic acid, 97 parts talc.
These dusts are formed by mixing the components then grinding the mixture to the desired particle size.
5% granules: 5 parts active compound, 0.25 part epichlorohydrin, 0.25 part cetyl polyglycol ether, 3.5 parts polyethylene glycol, 91 parts kaolin (particle size 0.3–0.8 mm)
Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo.

Wettable Powders 70 parts active compound, 5 parts sodium dibutylnaphthylsulfonate, 3 parts naphthalenesulfonic acid/phenosulfonic acid/formaldehyde condensate (3:2:1); 10 parts kaolin, 12 parts Champagne chalk.
40 parts active compound, 5 parts sodium lignin sulfonate, 1 part sodium dibutylnaphthalenesulfonic acid, 54 parts silicic acid.
25 parts active compound, 4.5 parts calcium lignin sulfate, 1.9 parts Champagne chalk/hydroxyethyl cellulose (1:1), 1.5 parts sodium dibutylnaphthalenesulfonate, 19.5 parts silicic acid, 19.5 parts Champagne chalk, 28.1 parts kaolin .

25 parts active compound, 2.5 parts isooctylphenoxypolyethylene-ethanol, 1.7 parts Champagne chalk-/hydroxyethyl cellulose (1.1), 8.3 parts sodium aluminum silicate, 16.5 parts kieselguhr, 46 parts kaolin.

10 parts active compound, 3 parts of a mixture of sodium salts of saturated fatty alcohol sulfates, 5 parts naphthalenesulfonic acid/formaldehyde condensate, 82 parts kaolin.

These wettable powders are prepared by intimately mixing the active compounds with the additives in suitable mixers, and grinding the resulting mixtures in mills or rollers 25% emulsifiable concentrate:

25 parts active substance, 2.5 parts epoxidized vegetable oil, 10 parts of an alkylarylsulfonate/fatty alcohol polyglycol ether mixture, 5 parts dimethylformamide, 57.5 parts xylene

What is claimed is:

1. A compound having the formula

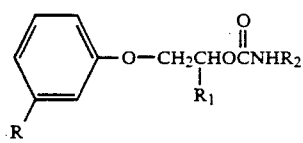

in which:
R is a member selected from the group consisting of trifluoromethyl, cyano, NO$_2$ and C$_1$-C$_3$ haloalkyloxy;
R$_1$ is selected from the group consisting of C$_1$-C$_4$ alkyl and C$_1$-C$_4$ haloalkyl; and
R$_2$ is selected from the group consisting of C$_1$-C$_4$ alkyl, C$_1$-C$_4$ alkoxy, C$_1$-C$_4$ alkoxyalkyl, C$_1$-C$_4$ haloalkyl and C$_1$-C$_4$ alkenyl.

2. A compound according to claim 1 wherein R is CF$_3$, R$_1$ is CH$_2$CH$_3$ and R$_2$ is CH$_2$CH=CH$_2$.

3. A compound according to claim 1 wherein R is CF$_3$, R$_1$ is CH$_2$CH$_3$ and R$_2$ is CH$_3$.

4. A compound having the formula

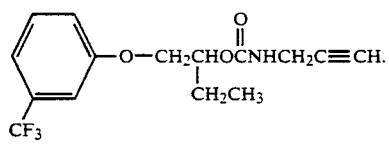

5. A compound according to claim 1 wherein R is CF$_3$, R$_1$ is CH$_2$CH$_3$ and R$_2$ is CH$_2$CH$_2$OCH$_3$.

6. A compound according to claim 1 wherein R is OCF$_3$, R$_1$ is CH$_2$CH$_3$ and R$_2$ is CH$_2$CH=CH$_2$.

7. An herbicidal composition comprising an herbicidally effective amount of a compound having the formula

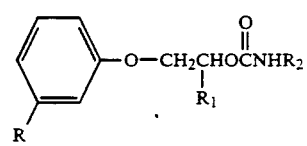

in which:
R is a member selected from the group consisting of trifluoromethyl, cyano, NO$_2$ and C$_1$-C$_3$ haloalkyloxy;
R$_1$ is selected from the group consisting of hydrogen, C$_1$-C$_4$ alkyl and C$_1$-C$_4$ haloalkyl;
R$_2$ is selected from the group consisting of C$_1$-C$_4$ alkyl, C$_1$-C$_4$ alkoxy, C$_1$-C$_4$ alkoxyalkyl, C$_1$-C$_4$ haloalkyl and C$_1$-C$_4$ alkenyl;
and an inert diluent carrier therefor.

8. An herbicidal composition according to claim 7 wherein R is CF$_3$, R$_1$ is CH$_2$CH$_3$ and R$_2$ is CH$_2$CH=CH$_2$.

9. An herbicidal composition according to claim 7 wherein R is CF$_3$, R$_1$ is CH$_2$CH$_3$ and R$_2$ is CH$_3$.

10. An herbicidal composition comprising an herbicidally effective amount of a compound having the formula

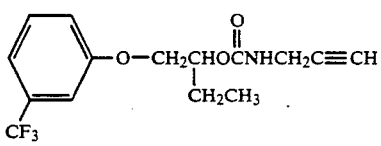

and an inert carrier therefor.

11. An herbicidal composition according to claim 7 wherein R is CF$_3$, R$_1$ is CH$_2$CH$_3$ and R$_2$ is CH$_2$CH$_2$OCH$_3$.

12. An herbicidal composition according to claim 7 wherein R is OCF$_3$, R$_1$ is CH$_2$CH$_3$ and R$_2$ is CH$_2$CH=CH$_2$.

13. A method of controlling undesirble vegetation comprising applying to said vegetation or to the locus thereof an herbicidally effective amount of a compound having the formula

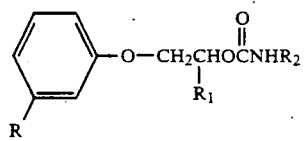

in which:
R is a member selected from the group consisting of trifluoromethyl, cyano, NO$_2$ and C$_1$-C$_3$ haloalkyloxy;
R$_1$ is selected from the group consisting of hydrogen, C$_1$-C$_4$ alkyl and C$_1$-C$_4$ haloalkyl; and
R$_2$ is selected from the group consisting of H, C$_1$-C$_4$ alkyl, C$_1$-C$_4$ ₖalkoxy, C$_1$-C$_4$ alkoxyalkyl, C$_1$-C$_4$ haloalkyl and C$_1$-C$_4$ alkenyl.

14. A method according to claim 13 wherein R is CF$_3$, R$_1$ is CH$_2$CH$_3$ and R$_2$ is CH$_2$CH=CH$_2$.

15. A method according to claim 13 wherein R is CF$_3$, R$_1$ is CH$_2$CH$_3$ and R$_2$ is CH$_3$.

16. A method of controlling undesirable vegetation comprising applying to said vegetation or to the locus thereof an herbicidally effective amount of a compound having the formula

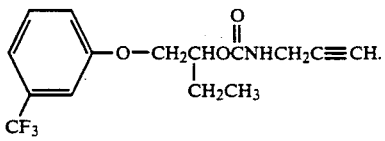

17. A method according to claim 13 wherein R is CF$_3$, R$_1$ is CH$_2$CH$_3$ and R$_2$ is CH$_2$CH$_2$OCH$_3$.

18. A method according to claim 13 wherein R is OCF$_3$, R$_1$ is CH$_2$CH$_3$ and R$_2$ is CH$_2$CH=CH$_2$.

* * * * *